US006369387B1

(12) United States Patent
Eckles

(10) Patent No.: US 6,369,387 B1
(45) Date of Patent: Apr. 9, 2002

(54) GAS ANALYZER

(75) Inventor: Robert D. Eckles, Malcolm, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

(21) Appl. No.: 09/419,020

(22) Filed: Oct. 15, 1999

(51) Int. Cl.[7] .......................... G01N 21/35; G01N 21/00
(52) U.S. Cl. ....................................... 250/343; 250/345
(58) Field of Search ................................. 250/343, 345

(56) References Cited

U.S. PATENT DOCUMENTS

| 3,270,756 | A | 9/1966 | Dryden |
| 3,712,325 | A | 1/1973 | Harnoncourt |
| 3,792,272 | A | 2/1974 | Harte et al. |
| 3,948,281 | A | 4/1976 | Strain et al. |
| 4,355,234 | A | 10/1982 | Fertig et al. |
| 4,395,632 | A | 7/1983 | Röss et al. |
| 4,467,213 | A | 8/1984 | Farren |
| 4,673,812 | A | 6/1987 | Yoneda |
| 4,738,147 | A | 4/1988 | Tomlin |

(List continued on next page.)

FOREIGN PATENT DOCUMENTS

| DE | 3525346 | 1/1987 |
| DE | 199 11 260 A1 | 3/1999 |
| EP | 0503511 B1 | 5/1998 |
| JP | 54-13388 | 1/1979 |
| JP | 55-109948 | 8/1980 |
| JP | 59-173734 | 10/1984 |
| JP | 62-217139 | 9/1987 |
| WO | WO 98/45686 | 10/1998 |

OTHER PUBLICATIONS

English–Language Abstract for DE19911260A1 (2 pages).
Partial European Search Report and Annex for EP00307471 (3 pages).
Jones et al. A Fast Response Atmospheric $CO_2$ Sensor for Eddy Correlation Flux Measurements, *Atmospheric Environment*, vol. 12, pp. 845–851, Pergamon Press Ltd. 1978.
Bingham et al., Development of a Miniature, Rapid–Response Carbon Dioxide Sensor, Progress Report from the NSF Ecosystem Program, The National Science Foundation, (Project DEB 77–16327), Mar. 20, 1978.
Brach et al., Open Path $CO_2$ Analyser, *The Institute of Physics*, vol. 6, pp. 1415–1419, 1981.
Altmann et al., Two–Mirrow Multipass Absorption Cell, *Applied Optics*, vol. 20, No. 6, pp. 995–999, Mar. 15, 1981.

(List continued on next page.)

Primary Examiner—Constantine Hannaher
Assistant Examiner—Andrew Israel
(74) Attorney, Agent, or Firm—Brinks Hofer Gilson & Lione

(57) ABSTRACT

In one preferred embodiment, a gas analyzer is presented that focuses light beams through gas cells without reflecting the light beams off the walls of the cells. By eliminating wall reflections, dirt or debris on the walls of the cells will not result in inaccurate gas concentration measurements. In another preferred embodiment, a gas analyzer is disclosed having removable gas cells, which allows a user to easily clean the cells instead of returning a contaminated gas analyzer to service personnel for cleaning. In yet another preferred embodiment, a gas analyzer has a purged gas flow channel between source and detector sections of the analyzer to remove contaminants that can result in inaccurate gas concentration measurements. In an additional preferred embodiment, a gas analyzer is disclosed which has a heat exchanger to equilibrate the temperature of incoming air to the temperature of the analyzer's gas cells, thereby avoiding temperature-based errors in gas concentration measurements.

35 Claims, 6 Drawing Sheets

U.S. PATENT DOCUMENTS

| | | | |
|---|---|---|---|
| 4,803,370 | A | 2/1989 | Eckles |
| 4,829,183 | A | 5/1989 | McClatchie et al. |
| 4,885,469 | A | 12/1989 | Yamagishi et al. |
| 4,914,719 | A | 4/1990 | Conlon et al. |
| 5,065,025 | A | 11/1991 | Doyle |
| 5,331,409 | A | 7/1994 | Thurtell et al. |
| 5,332,901 | A | 7/1994 | Eckles et al. |
| 5,340,987 | A | 8/1994 | Eckles et al. |
| 5,457,320 | A | 10/1995 | Eckles et al. |
| 5,468,961 | A | 11/1995 | Gradon et al. |
| 5,640,014 | A * | 6/1997 | Sauke et al. ................ 250/343 |
| 5,747,809 | A * | 5/1998 | Eckstrom .................... 250/343 |
| 5,811,812 | A | 9/1998 | Williams et al. |
| 6,037,592 | A * | 3/2000 | Sunshine et al. ........... 250/343 |

OTHER PUBLICATIONS

Heikinheimo et al., An Open Path, Fast Response IR Spectrometer for Simultaneous Detection of $CO_2$ and Water Vapor Fluctuations, *Journal of Atmospheric and Oceanic Technology*, vol. 6, pp. 624–636, Aug. 1989.

Bingham et al., Fast–Response Sensors for Eddy Covariance Measurements of $CO_2$ and Other Middle Infrared Absorbing Gases, Private Communication, not dated.

Bingham, Gail E., A Miniature Rapid Response Sensor for Atmospheric Concentrations of Carbon Dioxide, Private Communication, not dated.

Ohtaki, Eiji and Matsui, Tetuji, Infrared Device for Simultaneous Measurement of Fluctuations of Atmospheric Carbon Dioxide and Water Vapor, Boundary–Layer Meterology 24 (1982) 109–119.

Auble, David L. and Meyers, Tilden P., An Open Path, Fast Response Infrared Absorption Gas Analyzer for $H_2O$ and $CO_2$, Boundary–Layer Meterology 59: 243–256. 1992.

Internet Web page entitled Infrared Gas Analyzer, www.at-dd.noaa.gov/irga/irga.htm, Jul. 6, 1999.

Internet Web page entitled Advance Optima Infrared Analyzer Module Uras 14, www.hub.de/world/analyse/en/optima/p_aui_01.htm, Jul. 9, 1999.

Internet Web page entitled Dynamax Inc.—ADC 2250 Series, www.dynamax.com/adc.htm, Jul. 9, 1999.

Internet Web page entitled Infra–Red Gas Analysis Systems CIRAS–1, CIRAS–2 SC & DC, www.ppsystems.com/gas2.html, Jul. 9, 1999.

Internet Web page entitled Gas Analysis Ultramat 6, www3.ad.siemens.de/ca01cache/en_3000133_b_tab0_IE4.htm, Jul. 9, 1999.

Internet Web page entitled Gas Analysis Ultramat 23, www3.ad.siemens.de/ca01cache/en_3000134_b_tab01_IE4.htm, Jul. 9, 1999.

Internet Web page entitled Gas Analysis Ultramat 5F–Ex u. 5F–2R–Ex, www3.ad.siemens.de/ca01cache/en_3000137_b_tab0_{13} IE4.htm, Jul. 9, 1999.

Internet Web page entitled Gas Analysis Ultramat/Oxymat 6, www3.ad.siemens.de/ca01cache/en_3000154_b_tab0_IE4.htm, Jul. 9, 1999.

"Infrared Gas Analyzers for $CO_2$ and $CO_2/H_2O$ Measurements," LI–COR, 15 pages (1994).

* cited by examiner

GAS ANALYZER

BACKGROUND

The increasing carbon dioxide concentration in the atmosphere and the resulting greenhouse effect and climate change have become compelling topics for scientific research. In order to understand the global carbon balance, it is necessary to determine the rate at which carbon dioxide and energy exchanges between the atmosphere and terrestrial and oceanic ecosystems. A measurement technique called "eddy covariance" has been widely used to determine these rates. The air just above the earth's surface is turbulent, and small parcels of air called "eddies" transport carbon dioxide, water vapor, and heat between the atmosphere and the surface. These transport rates can be calculated from simultaneous, high-frequency measurements of the vertical component of wind speed, the concentrations of carbon dioxide and water vapor, and the air temperature.

To measure concentrations of carbon dioxide and water vapor, a gas analyzer can be used to analyze the transmittance of light in appropriate wavelength bands through a gas sample. With some gas analyzers, a sample gas containing unknown gas concentrations of carbon dioxide and water vapor is placed in a sample cell, and a reference gas with zero or known concentrations of carbon dioxide and water vapor is placed in a reference cell. The analyzer measures the unknown gas concentrations in the sample cell from calibrated signals that are proportional to the difference between light transmitted through the sample cell and light transmitted through the reference cell.

In eddy covariance applications, ambient air that is full of dust and pollen must be moved through the analyzer at high flow rates in order for the analyzer to have the necessary frequency response. Even when the air is filtered, contamination of the sample cells is inevitable, requiring the analyzer to be returned to the factory for cleaning. This is an expensive and time-consuming process, especially when the analyzer is used in a remote location such as the Amazon basin, the north slope of Alaska, or the deserts of Africa.

There is a need, therefore, for an improved gas analyzer.

SUMMARY

The present invention is defined by the following claims, and nothing in this section should be taken as a limitation on those claims.

By way of introduction, the preferred embodiments described below provide an improved gas analyzer that overcomes the problems described above. In one preferred embodiment, a gas analyzer is presented that focuses light beams through gas cells without reflecting the light beams off the walls of the cells. By eliminating wall reflections, dirt or debris on the walls of the cells will not result in inaccurate gas concentration measurements. In another preferred embodiment, a gas analyzer is disclosed having removable gas cells, which allows a user to easily clean the cells instead of returning a contaminated gas analyzer to service personnel for disassembly, cleaning, and re-assembly. In yet another preferred embodiment, a gas analyzer with a purged gas flow channel is described. In this preferred embodiment, purged gas flows between source and detector sections of the analyzer, ensuring that the source and detector sections are free of contaminants that can result in inaccurate gas concentration measurements. In an additional preferred embodiment, a gas analyzer is disclosed which has a heat exchanger to equilibrate the temperature of incoming air to the temperature of the analyzer's gas cells, thereby avoiding temperature-based errors in gas concentration measurements.

The preferred embodiments will now be described with reference to the attached drawings.

DETAILED DESCRIPTION OF THE PRESENTLY PREFERRED EMBODIMENTS

Operational Overview

By way of introduction, the gas analyzer of the presently preferred embodiments generally comprises a light source, a sample cell, a reference cell, and two detectors. The gas analyzer can be used to measure a concentration of one or more gases that have a high absorbance at different wavelength bands. For example, in one application, the gas analyzer can be used to measure a concentration of $CO_2$ and water vapor in a sample gas. Generally, the gas analyzer uses non-dispersive infrared (NDIR) absorption to measure concentration of a gas in a sample cell based on the difference between absorption of infrared radiation passing through the sample and reference cells.

In operation, the light source transmits light having a spectrum of wavelengths through the sample and reference cells. Gases present in the sample and reference cells absorb light at different wavelength bands. For example, $CO_2$ has a high absorbance at 4.255 $\mu$m, and water vapor has a high absorbance at 2.595 $\mu$m. Light exiting the sample and reference cells is detected by the two detectors. One of the detectors is sensitive to wavelength bands absorbed by one of the gases (e.g., $CO_2$), and the other detector is sensitive to wavelength bands absorbed by the other gas (e.g., water vapor). When the reference cell contains a known absorber-gas concentration, the concentration of the gases in the sample cell can be determined by calculating the difference between absorption in the sample cell and the reference cell. When the reference cell contains a non-absorber gas, the signal detected in the sample cell is compared to the signal detected in the reference cell to provide an absolute measurement of gas concentration in the sample cell.

As described in the Background section above, contamination of the gas analyzer can result in inaccurate concentration measurements. Contamination can occur in the sample and reference cells and can occur in the sections of the gas analyzer that house the light source and detectors. Additionally, inaccurate concentration measurements can result due to fluctuations in gas temperature. The following preferred embodiments offer solutions to these problems. It is important to note that any of these preferred embodiments can be used alone or in combination with one another.

Optical Path Embodiments

Figure 1:
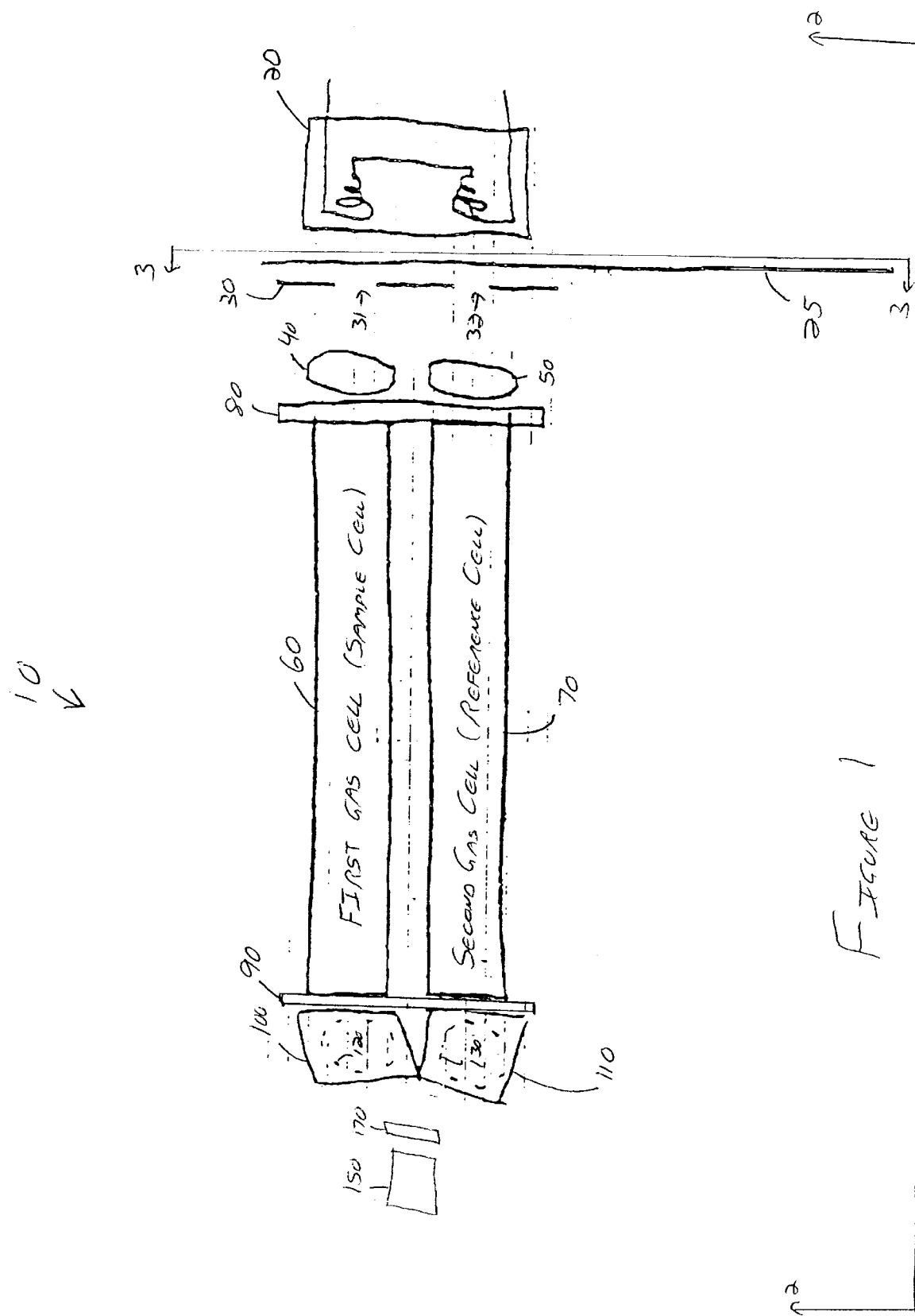
FIG. 1 is a diagram of a gas analyzer of a presently preferred embodiment.

Turning now to the drawings, FIG. 1 is a diagram of a gas analyzer 10 of a presently preferred embodiment. The gas analyzer 10 comprises a light source 20, a light disrupter 25, a spatial filter 30, first and second lenses 40, 50, a first gas cell 60, a second gas cell 70, and first and second windows 80, 90 sealing the first and second gas cells 60, 70. The gas analyzer 10 also comprises a first and second mirror 100, 110, third and fourth lenses 120, 130, a beam splitter 140, and first and second detectors 150, 160 with first and second filters 170, 180 (see FIG. 2).

The light source 20 preferably comprises a one-filament twin-coil design with a 0.010 inch diameter tungsten wire. The filament is heated to emit infrared radiation over a wide spectral band including longer wavelengths and shorter wavelengths, which in this preferred embodiment are suitable for measuring carbon dioxide and water vapor. The filament is preferably maintained at a constant color temperature of 1250 K by a light-sensing photodiode, which is part of a feedback circuit that controls the power used to heat the source. This design ensures a highly-stable source of radiation. For long life and added stability, the light source 20 is preferably vacuum-sealed with a sapphire window, which allows transmission of light at the wavelengths of interest.

Figure 3:
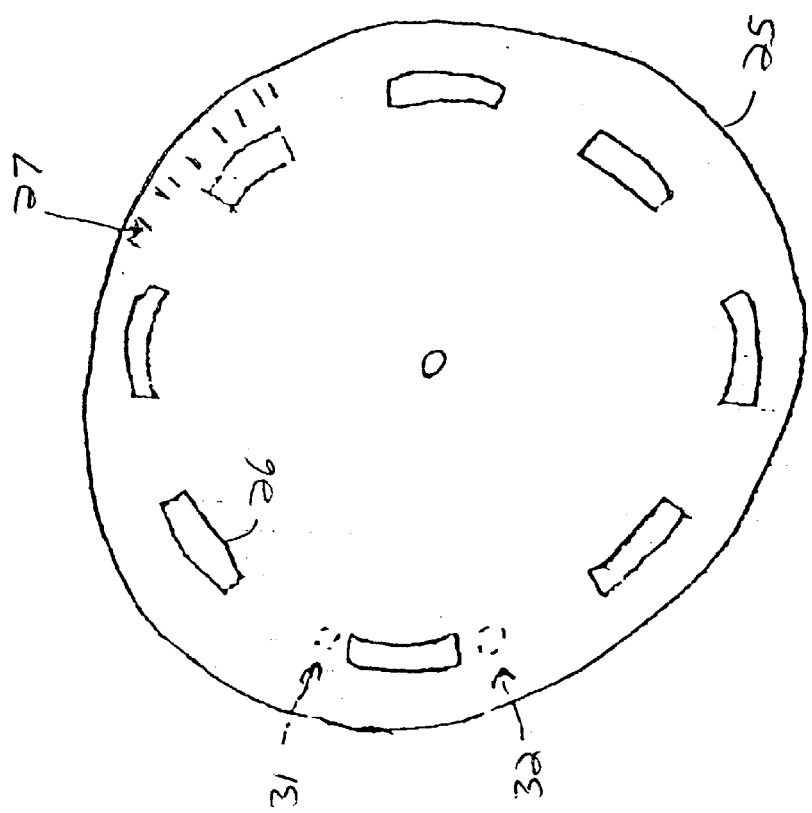
FIG. 3 is a diagram of a light disrupter of the gas analyzer of FIG. 1.

Light emitted from the light source 20 is transmitted to the light disrupter 25, which alternately transmits light through the first and second gas cells 60, 70. For simplicity, the term "light disrupter" is intended to broadly refer to any device that is operative to disrupt transmission of light from the light source 20 to the first and second gas cells 60, 70. For example, a light disrupter can be a device that intermittently disposes an object between the light source 20 and one of the gas cells 60, 70. In this preferred embodiment, the light disrupter 25 takes the form of a chopping shutter disc rotated by a motor 28, which is preferably a brushless DC motor that rotates at 4,500 revolutions per minute. With reference to FIG. 3, the chopping shutter disc 25 is preferably a four-inch diameter wheel with eight major openings 26 and 512 minor openings 27, only some of which are shown in FIG. 3. The minor openings 27 are used as timing slots to control the speed of the chopping shutter disc 25 using a conventional feedback loop. The minor openings 27 are also used to provide timing signals to a concentration calculating system (not shown) to identify relevant measurement signals. The major openings 26 are used to alternately transmit infrared radiation from the light source 20 to the first and second gas cells 60, 70. This modulates the transmitted light at a high chopping frequency, resulting in reduced sensitivity of the detectors 150, 160 to low frequency vibrations. Additionally, using a larger number of major openings 26 increases the motor's life by providing high chopping frequency at lower motor speeds.

Light passing through the major openings 26 of the light disrupter 25 passes through first and second apertures 31, 32 of the spatial filter 30 as the major openings 26 scan past the apertures 31, 32. The first and second lenses 40, 50 focus light transmitted though the apertures 31, 32 for transmission through the first and second gas cells 60, 70. By using two lenses instead of a single lens covering both cells 60, 70 and by positioning and sizing the apertures 31, 32 to coincide with the focal point of the first and second lens 40, 50, light beams can be transmitted though the cells 60, 70 without contacting the interior surface of the cells 60, 70, as shown by the dashed lines in FIG. 2. Since the light beams are focused at the opposite end of the cells 60, 70 and do not reflect off the walls of the cells 60, 70, dirt or debris on the walls of the cells 60, 70 will not result in inaccurate concentration measurements, unlike other gas analyzers.

The apertures 31, 32 in the spatial filter 30 can be positioned and sized based on the focal length of the light beam, the desired diameter of the light beam, and the length of the first and second gas cells 60, 70 to define the light beam's field of view or "f-stop." In this preferred embodiment, the apertures 31, 32 are preferably 0.050 inch-diameter holes in a 0.005 inch-thick spatial filter 30. Also, while the spatial filter 30 is positioned between the light disrupter 25 and the first and second lenses 40, 50 in FIGS. 1 and 2, it should be noted that the spatial filter 30 can instead be positioned between the light source 20 and the light disrupter 25. Additionally, one or more than one spatial filter can be used. Further, the spatial filter 30 shown in FIG. 1 can be considered a single spatial filter with two apertures or a first and second spatial filter, each with its own aperture.

Gases present in the cells 60, 70 absorb light at different wavelength bands. For example, $CO_2$ absorbs light at about 4.25 $\mu$m, and water vapor absorbs light at about 2.59 $\mu$m. Light exiting the cells 60, 70 is reflected by the first and second mirrors 100, 110, respectively, and is focused by the third and fourth lenses 120, 130, respectively.

Figure 2:
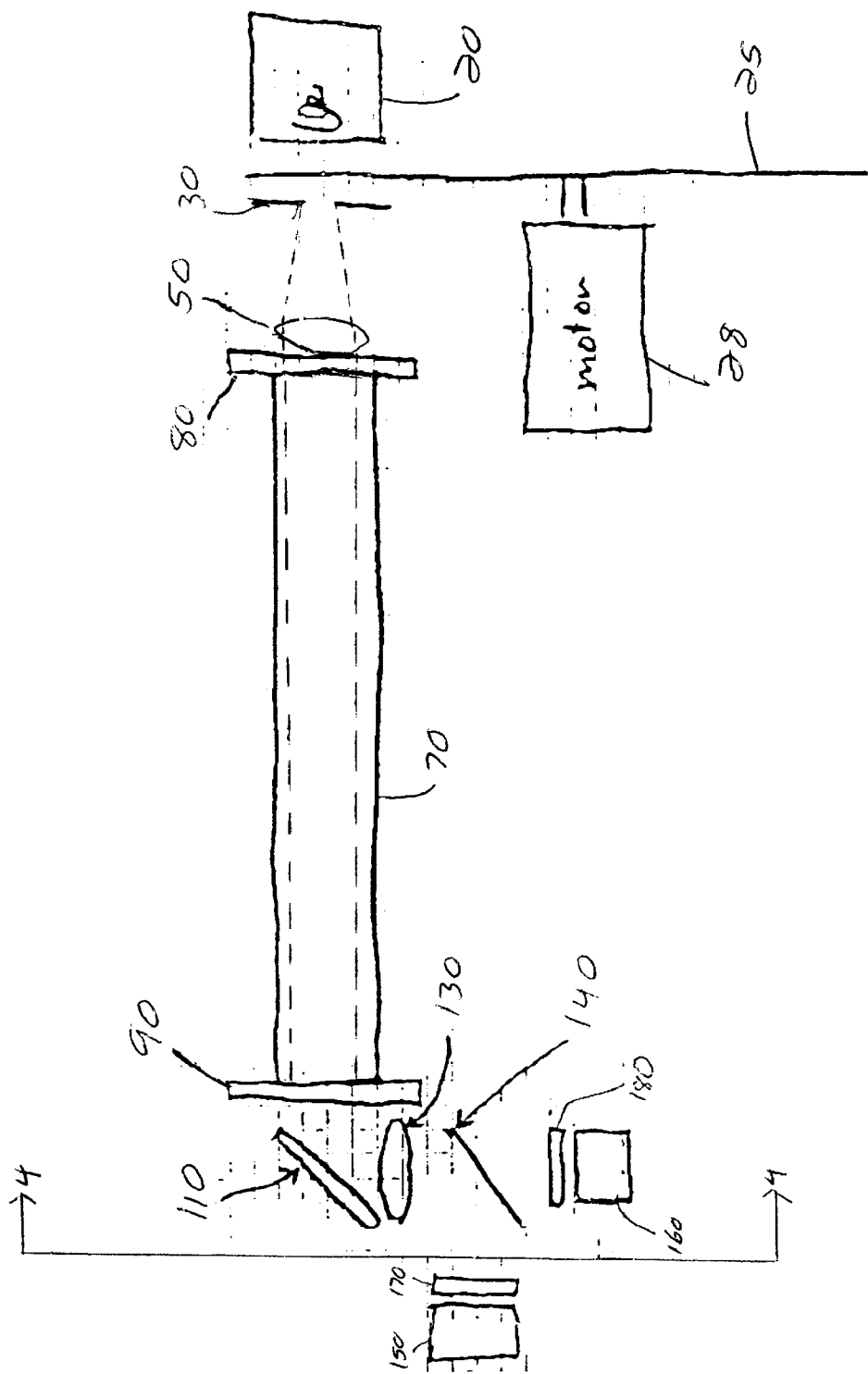
FIG. 2 is a side view of the gas analyzer of FIG. 1.
Figure 4:
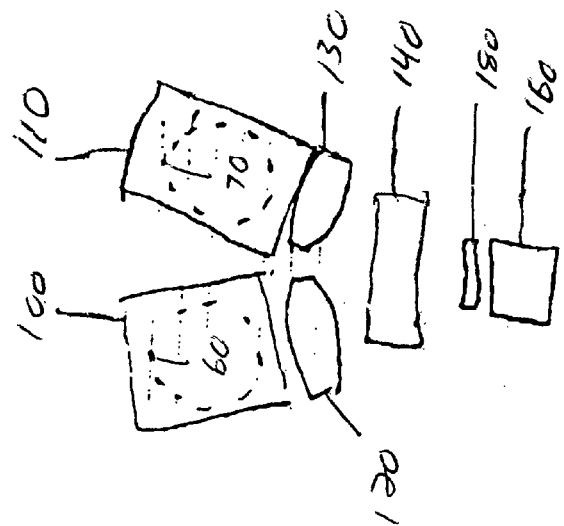
FIG. 4 is an end view of the gas analyzer of FIG. 1.

As best shown in FIGS. 2 and 4, it is preferred that the first and second mirrors 100, 110 be tilted at a 45-degree angle to bend the exiting light at a 90-degree angle and that the first and second mirrors 100, 110 and the third and fourth lenses 120, 130 be rotated at a 17-degree angle to lay the beams exiting the first and second gas cells 60, 70 on top of one another so that they intersect at the detectors 150, 160. In this way, the detectors 150, 160 can intercept the light exiting both cells 60, 70. The mirrors 100, 110 preferably have a gold surface protection that allows greater than 96% reflectance at 4 $\mu$m and preferably have the following dimensions: 1 inch×0.75 inches×0.02 inches. It is also preferred that the lenses 40, 50, 120, 130 be made from CaF2 and have an effective focal length of 0.75 inches and a diameter of 0.5 inches.

The beam splitter 140 transmits light of longer wavelengths and reflects light of shorter wavelengths. The beam splitter 140 is preferably a 0.02 inch thick, 0.75 inch diameter dichroic beam splitter with a greater than 70% transmission of 3.5 to 4.5 $\mu$m and a greater than 80% reflection of 2 to 2.7 $\mu$m at a 45-degree angle of incidence.

Light reflected by the beam splitter 140 is filtered by the first filter 170 before reaching the first detector 150, and light transmitted by the beam splitter 140 is filtered by the second filter 180 before reaching the second detector 160. The first and second filters 170, 180 are preferably infrared bandpass filters with the following dimensions: 0.25 inches×0.25 inches×0.02 inches. The first filter 170 preferably has a center wavelength of 2.595 $\mu$m and a bandwidth of 0.05 $\mu$m (for water vapor), and the second filter 180 preferably has a center wavelength of 4.255 $\mu$m and a bandwidth of 0.15 $\mu$m (for $CO_2$). It is preferred that the detectors 150, 160 be 1 mm×1 mm lead selenide detectors. It is further preferred that the detectors 150, 160 have a thermoelectric cooler to reduce temperature-dependent noise. In an alternate embodiment, instead of using two detectors, a single detector with replaceable filters (such as on a filter wheel) is used.

As described in the Operational Overview section above, the gas analyzer 10 uses non-dispersive infrared (NDIR) absorption to measure concentration of a gas in a sample cell 60 based on the difference between absorption of infrared radiation passing through the sample and reference cells 60, 70. $CO_2$ in the cells 60, 70 absorbs the transmitted light at about 4.26 $\mu$m, and water vapor absorbs the transmitted light at about 2.59 $\mu$m. The first and second filters 170, 180 in series with the first and second detectors 150, 160 allow the first detector 150 to sense the carbon dioxide absorption and the second detector 160 to sense water vapor absorption.

When the reference cell 70 contains a known absorber-gas concentration, the concentration of the gases in the sample cell 60 can be determined by calculating the difference between absorption in the sample cell 60 and absorption in the reference cell 70. When the reference cell 70 contains a gas with a non-absorber gas (such as when the air supplied to the reference cell 70 has been scrubbed of $CO_2$), the signal detected in the sample cell 60 is compared to the non-absorber gas signal to provide an absolute measurement of gas concentration in the sample cell 60. To eliminate errors due to components of the analyzer (e.g., strength of the source, transmission of light through the filter, and responsivity of the detector), it is preferred that the ratio of the transmittance of the sample and reference cells be used to calculate the absorption of the sample gas relative to the reference gas. By using ratios instead of differences, component-based errors can be eliminated.

In an alternate embodiment, instead of measuring concentration using the difference between sample and reference gases, the concentration of a gas in each cell can be measured with respect to a known absorber-gas concentration that was in the same cell at some previous time. In this way, simultaneous measurement of absolute and differential gas concentrations can be made without knowing reference gas concentrations. In this embodiment, instead of taking the ratio of sample to reference gas, the ratio of data to calibrated value is taken. The calibrated value can be obtained by using a gas mixture that does not contain the gas of interest (e.g., $CO_2$). This differential-absolute-reference mode allows the analyzer to be used as two absolute analyzers, one differential analyzer, or one absolute analyzer and one differential analyzer.

Removable Gas Cell Embodiments

Figure 5:
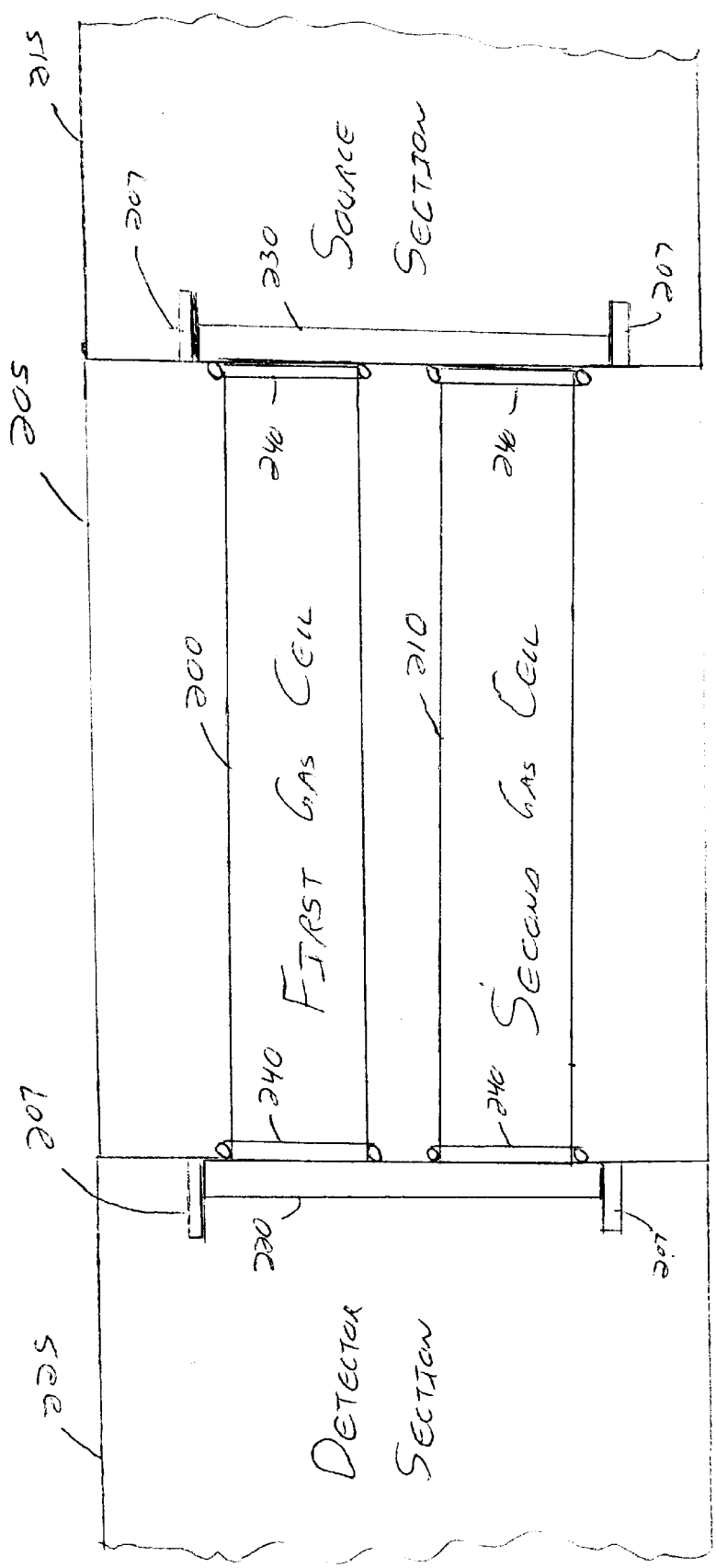
FIG. 5 is a sectional view of a gas analyzer of another presently preferred embodiment.

Turning again to the drawings, FIG. 5 shows a sectional view of a gas analyzer of another presently preferred embodiment. In this preferred embodiment, first and second gas cells 200, 210 are disposed in a housing 205. The housing 205 in which the gas cells 200, 210 are disposed is secured to the gas analyzer by locator members 207. In this preferred embodiment, there are four locator members 207, each made of stainless steel and each ⅛ inches in diameter and ⅛ inches long. It should be noted that any suitable number of locator members can be used and that the material and dimensions of the locator members can be varied.

The gas cells 200, 210 are coupled with a source section 215 and a detector section 225 to form a rigid, integral source-optical path-detector assembly, such that ambient air (which may contain contaminants) does not flow between the source and detector sections 215, 225 and the gas cells 200, 210. The components of the source and detector sections 215, 225 (such as the light source and detectors) are not shown for simplicity. Disposed between the source and detector sections 215, 225 and the gas cells 200, 210 are first and second windows 220, 230. The first and second windows 220, 230 are sealed against the cells with a set of sealing members 240 to prevent contaminants from entering the cells 200, 210. The set of sealing members 240 is formed to allow the housing 205 and the first and second gas cells 200, 210 to be removed from the first and second windows 220, 230. This allows a user of the gas analyzer to remove and clean the gas cells 200, 210 in the field. When the gas cells 200, 210 are placed back into the analyzer, the locator members 207 on the housing 205 ensure proper placement of the gas cells 200, 210, allowing the gas cells 200, 210 to be reassembled into the analyzer without recalibration.

As used herein, a "set of sealing members" refers to one sealing member or a plurality of sealing members. In the presently preferred embodiment shown in FIG. 5, the "set of sealing members" takes the form of four o-rings. It is preferred that the o-rings be a 013-type o-ring having a 7/16 inch inner diameter and a 0.070 inch thickness. Because o-rings are used as sealing members in this preferred embodiment, the gas cells 200, 210 are shaped as two separate round components. Each cell 200, 210 is preferably 6 inches long with a 0.375 inch diameter, and each window 80, 90 is preferably a 1.375 inch diameter, 0.063 inch-thick synthetic sapphire window. It should be noted that the shape and size of the cells and/or sealing members can be varied.

Purged Gas Flow Embodiments

A gas analyzer can become contaminated when gases present in the source and detector sections absorb light at the same wavelengths as the gases present in the sample and reference cells. In this situation, it is unclear whether the detected absorption is due to the presence of gas in the sample and reference cells or due to the contaminant. As a result, the calculated concentration of gas may be inaccurate. To ensure that the source and detector sections are free of contaminants, the gas analyzer of FIG. 6 comprises two purged gas flow channels 320, 330 coupling the source and detector sections 300, 310, which enable purged gas to flow between the source and detector sections 300, 310. The components of these sections 300, 310 (such as the light source and detectors) are not shown for simplicity. The gas analyzer also comprises a purged gas circulation device 340 that circulates purged gas through the flow channels 320, 330, as shown by the arrows in FIG. 6. By circulating purged gas between the source and detector sections 300, 310, contaminants present in the source and detector sections that absorb light at the relevant wavelengths can be removed.

Figure 6:
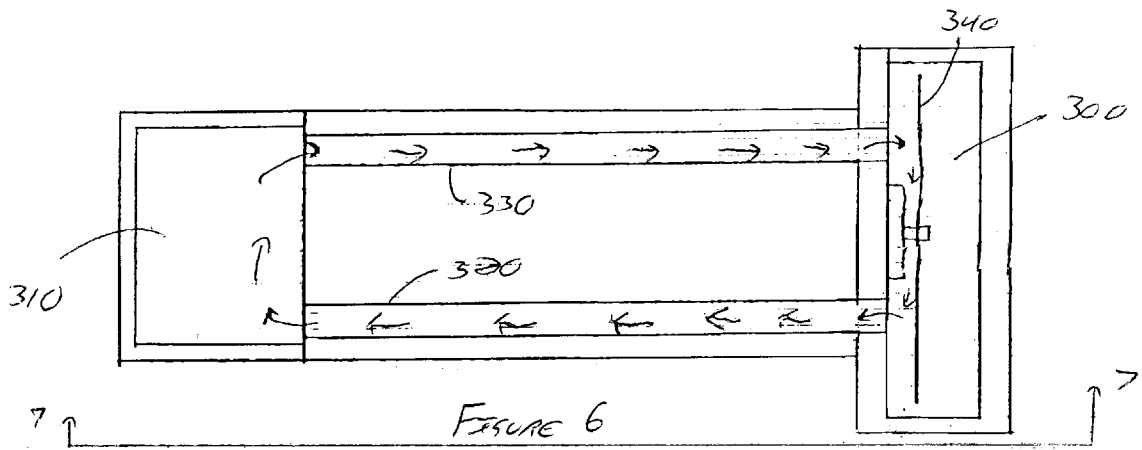
FIG. 6 is a diagram of a gas analyzer of another presently preferred embodiment.
Figure 7:
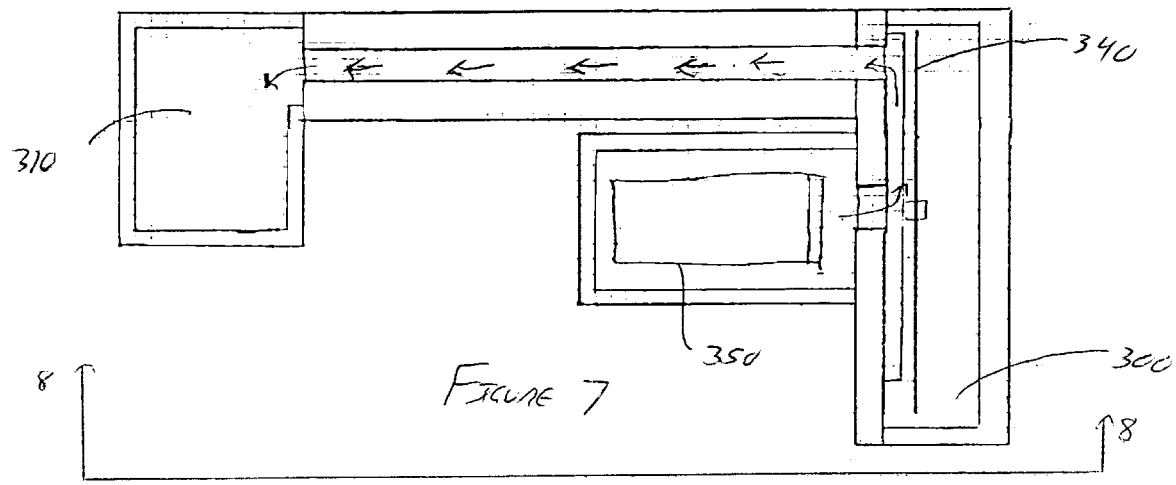
FIG. 7 is a side view of the gas analyzer of FIG. 6.
Figure 8:
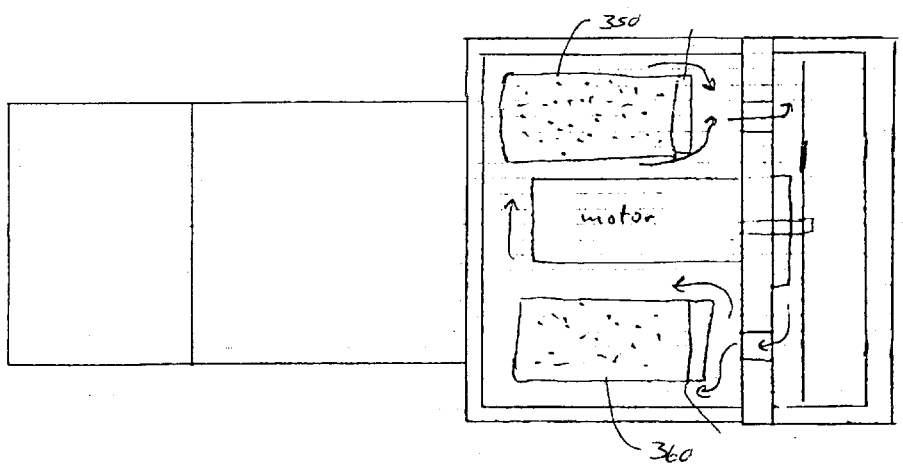
FIG. 8 is a side view of the gas analyzer of FIG. 7.

FIG. 7 is a side view of the gas analyzer of FIG. 6 and shows a purged gas provider 350 providing purged gas to the source section 300. In this preferred embodiment, the purged gas provider 350 takes the form of a single container having an inlet and outlet conduit with the appropriate chemicals between them, preferably in two compartments. One of the chemicals is preferably soda lime (a $CO_2$ scrubber), and the other chemical is preferably magnesium perchlorate (an $H_2O$ desiccant). In this preferred embodiment, air enters the purged gas provider 350, flows through the soda lime (which removes $CO_2$), then flows through the magnesium perchlorate (which removes $H_2O$ vapor), and then flows out of the purged gas provider 350. Because the purged gas flow channels 320, 330 couple the source and detector sections 300, 310, a single purged gas provider 350 can be used for both the source and detector sections 300, 310. In this preferred embodiment, two containers 350, 360, each containing the two chemicals, are used (see FIG. 8).

In this preferred embodiment, the first and second gas cells as well as the flow channels 320, 330 are disposed in a single housing, thereby providing a solid optical path. Also, in the preferred embodiments shown in FIGS. 6 and 7, the purged gas circulation device 340 is located in the source section 300 and is the chopping shutter disc described above. It should be noted that the purged gas circulation device can take any form and can be located in the detector section 310 or located external to the source and detector sections 300,310. However, it is preferred that the purged gas circulation device be in the source section 300 rather than in the detector section 310. It should also be noted that fewer or more than two purged gas flow channels can be used. Further, while the purged gas provider 350 is shown as being internal to the source section 300, the purged gas provider 350 can also be located in the detector section 310 or external to both the source and detector sections 300, 310.

Heat Exchanger Embodiments

Inaccurate gas concentration measurements can occur if gas entering a gas analyzer is not at the same temperature as the analyzer's gas cells since measured $CO_2$ and water vapor concentrations are proportional to temperature. For example, in eddy covariance applications, carbon dioxide transport rates are computed from high frequency fluctuations in the measured gas concentration and wind speed. Correlated fluctuations in the temperature of air flowing through the analyzer will cause density changes that can generate erroneous results.

Figure 9:
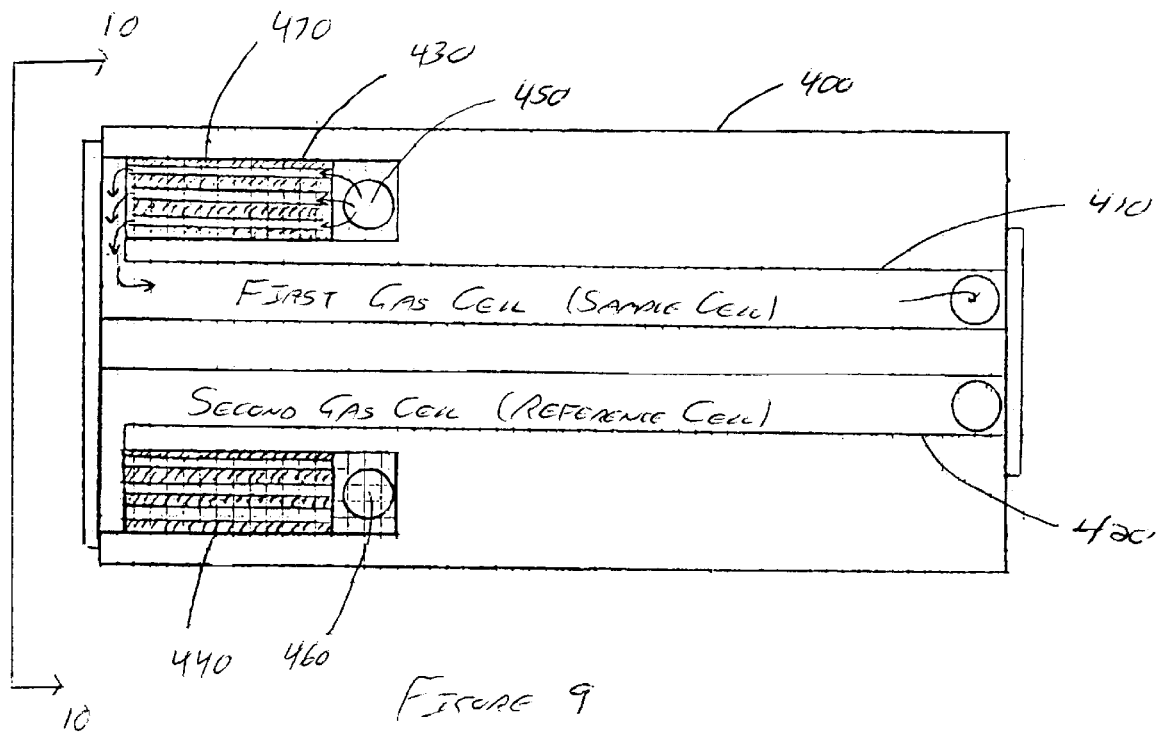
FIG. 9 is a diagram of a housing of a gas analyzer of another presently preferred embodiment.
Figure 10:
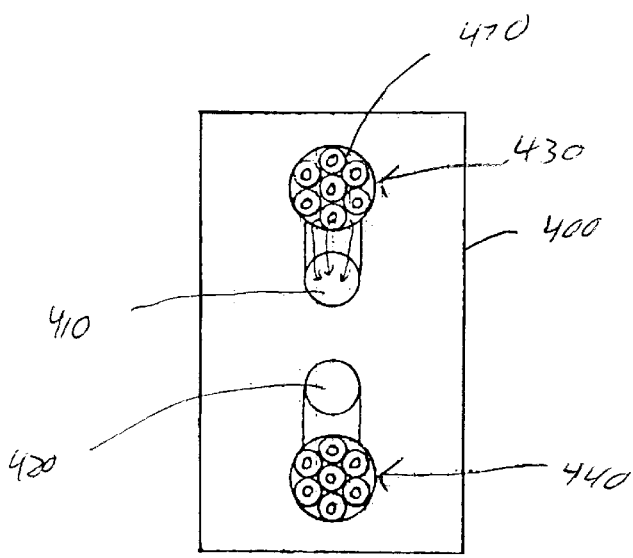
FIG. 10 is a side view of the housing of FIG. 9.
Figure 2:
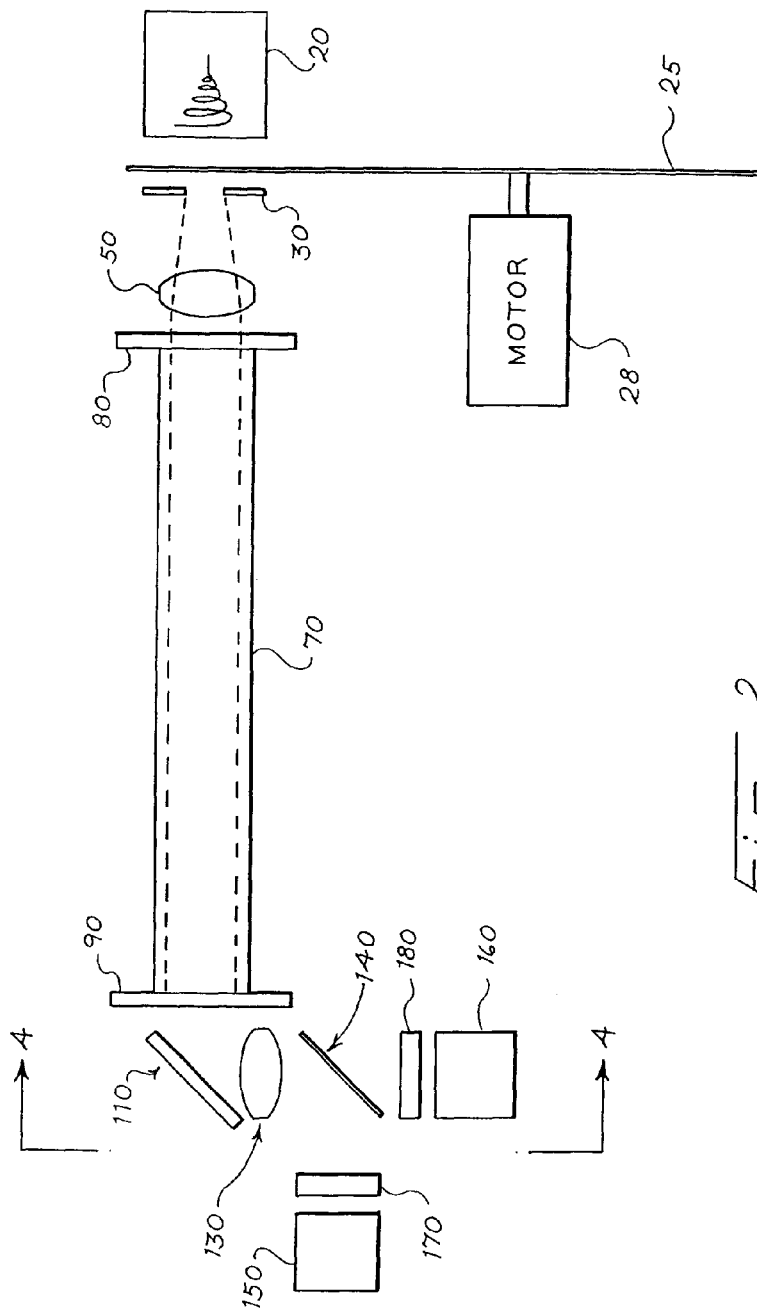
Figure 4:
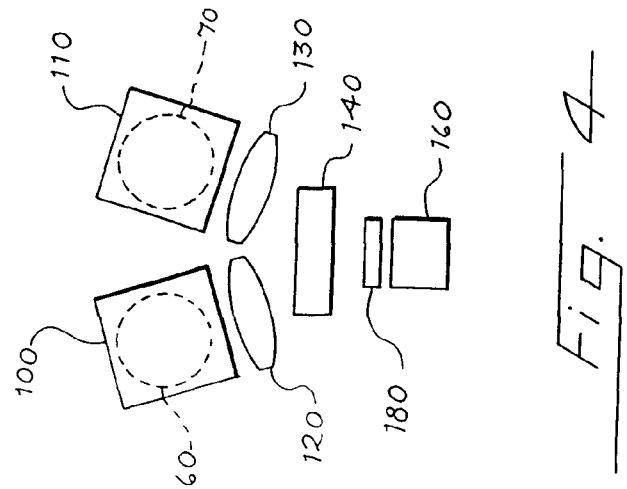
Figure 3:
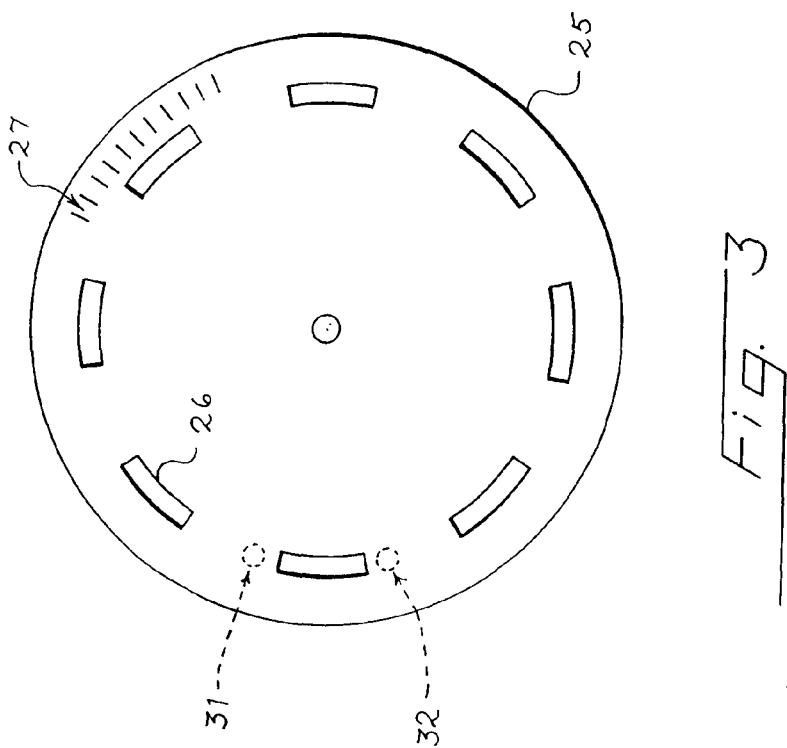
Figure 5:
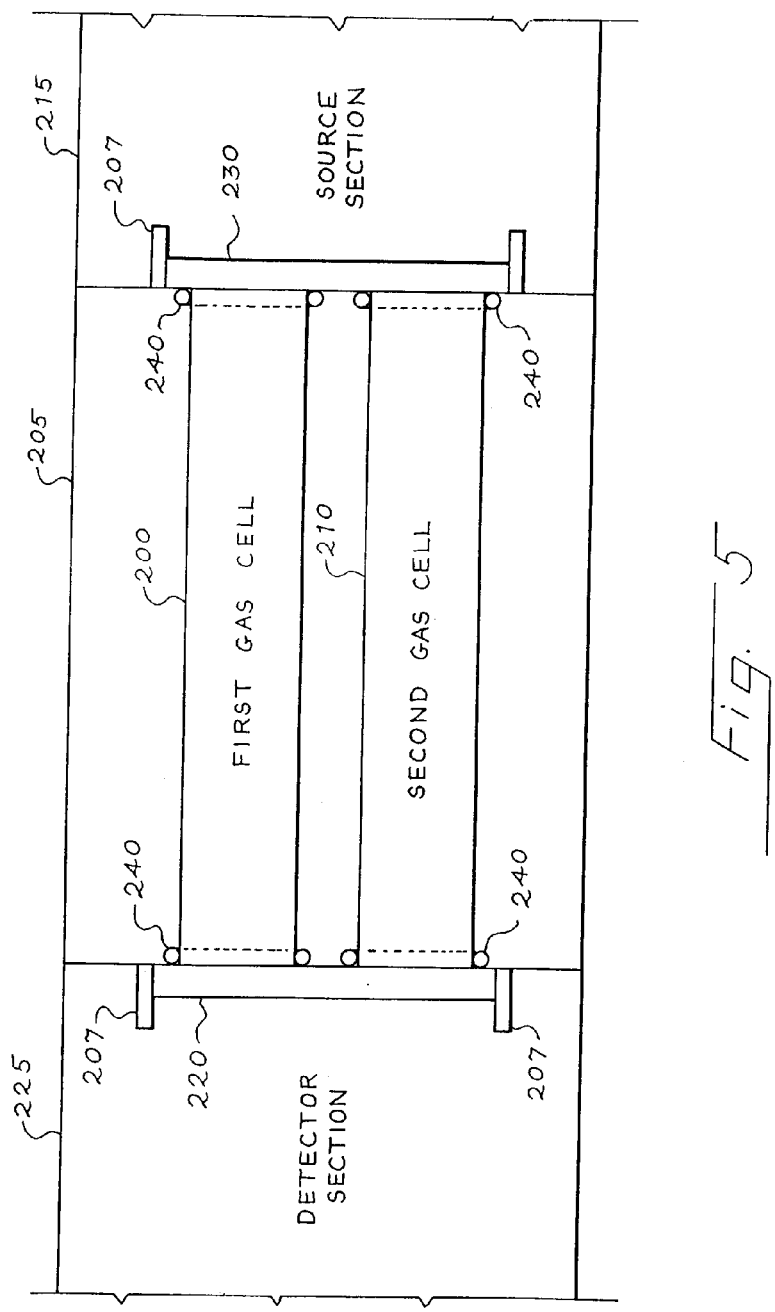
Figure 9:
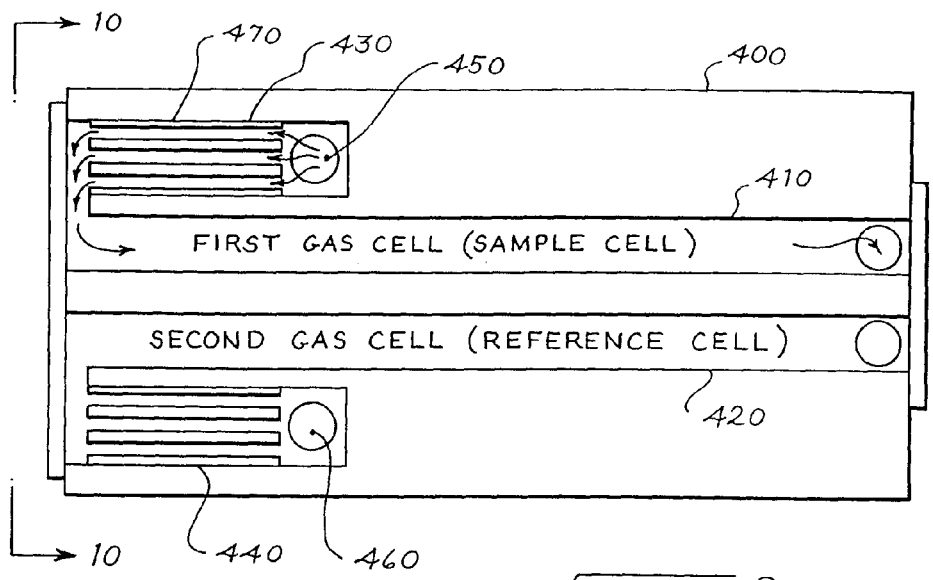
Figure 10:
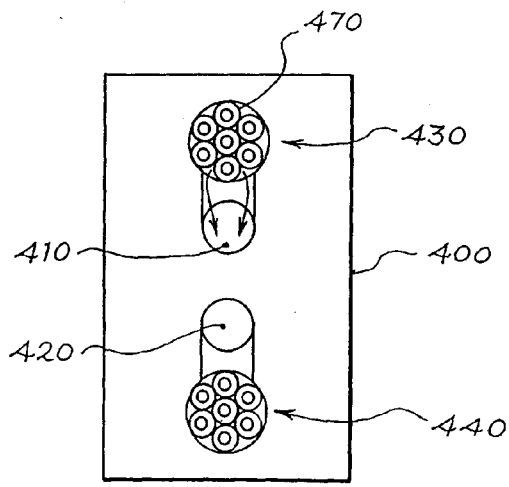

FIG. 9 presents a diagram of a gas analyzer that overcomes this problem by bringing the incoming air to a constant temperature (preferably, to the same temperature as the analyzer's gas cells) before the air enters the analyzer's gas cells. The gas analyzer of FIG. 9 comprises a solid optical path in which first and second gas cells 410, 420 are disposed in a housing 400. Also disposed in the housing 400 are first and second inlet portions 430, 440, which allows incoming air to flow from first and second inlet ports 450, 460 to the first and second gas cells 410, 420, respectively. Disposed in the first and second inlet portions 430, 440 is a heat exchanger 470 that is operative to equilibrating a temperature of incoming air to a temperature of the housing 400. As best shown in FIG. 10, the heat exchanger 470 of this preferred embodiment takes the form of a plurality of tubing tightly compressed with each other and into the first and second air inlet portions 430, 440.

Because the outside edges of the tubing is in high-pressure contact with the housing 400, the thermal conductance of the tubing tends to equilibrate the temperature of the air flowing in and around the tubing to the temperature of the housing 400. Specifically, air flowing in and around the tubing is forced into a small flow thickness across a large surface area, thus providing rapid heat exchange. Accordingly, because the heat exchanger 470 equilibrates the temperature of air flowing to the cells 410, 420 to the temperature of the cells 410, 420, temperature-based errors in gas concentration measurements are avoided. To allow the heat exchanger 470 to keep the gas temperature constant and equal to the cell temperature, it is preferred that the gas cells 410, 420 have a large thermal mass to accomplish this task. Thus, the solid optical path not only provides physical stability, but also provides a uniform thermal cross section. Another advantage associated with this preferred embodiment is that a single temperature sensor can be used to measure the average temperature of the optical bench. The gas analyzer can report failure of this temperature sensor to the user via a visual and/or audible signal.

It is preferred that the housing 400 be a solid aluminum block and that the tubing be made of soft copper. It is also preferred that each copper tube have an outer diameter of ⅛ inch and inner diameter of ¹⁄₁₆ inch, with a length of 1.5 inches. Preferably, the first and second inlet portions 430, 440 have a length of 1.5 inches and an inner diameter of 0.375 inches, such that seven copper tubes are compressed in each inlet portion. It is further preferred that the sources of air to the first and second gas cells 410, 420 be directly connected to the inlet ports 450, 460 without tubing. By eliminating the use of tubing, the disadvantages associated with tubing (e.g., pressure drop, gas diffusion, gas absorption, and turbulence) are also eliminated.

In addition to measuring the concentration of $CO_2$ and/or water vapor, the gas analyzers of these preferred embodiments can also be used to measure the concentration of other gases, such as, but not limited to, nitrogen oxide, carbon monoxide, and methane. In this regard, the gas analyzer can have single or multiple (two or more) gas cells.

The gas analyzer of these preferred embodiments can have any appropriate data output, such as, but not limited to, an LCD display, uncalibrated or calibrated voltage outputs, current loop outputs, and RS-232C serial output. In addition to outputting data, an RS-232C serial output can be used to receive remote commands from an RS-232C terminal or computer. Further, the gas analyzers of these preferred embodiments can be used in any suitable application, such as photosynthesis measurements, global warming studies (atmospheric chemistry), ecology, forestry, agronomy, oceanography, environmental studies, bioremediation, and jet engine testing. Also, the gas analyzers of these preferred embodiments can be built as portable units that are easily transportable for field use.

It is important to note that any of the various aspects of the preferred embodiments can be used alone or in combination. Additionally, it should be understood that any appropriate hardware, analog or digital, and/or any appropriate software language can be used in the operation of the gas analyzer.

U.S. Pat. No. 5,340,987 and U.S. patent application Ser. No. 09/397,903 (filed Sep. 17, 1999), both of which are assigned to the assignee of the present application, are hereby incorporated by reference herein.

It is intended that the foregoing detailed description be understood as an illustration of selected forms that the invention can take and not as a definition of the invention. It is only the following claims, including all equivalents, that are intended to define the scope of this invention.

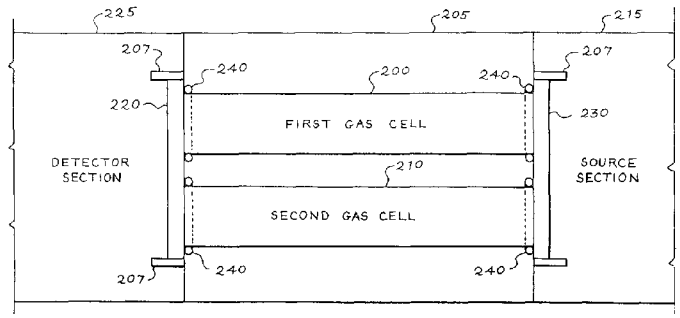

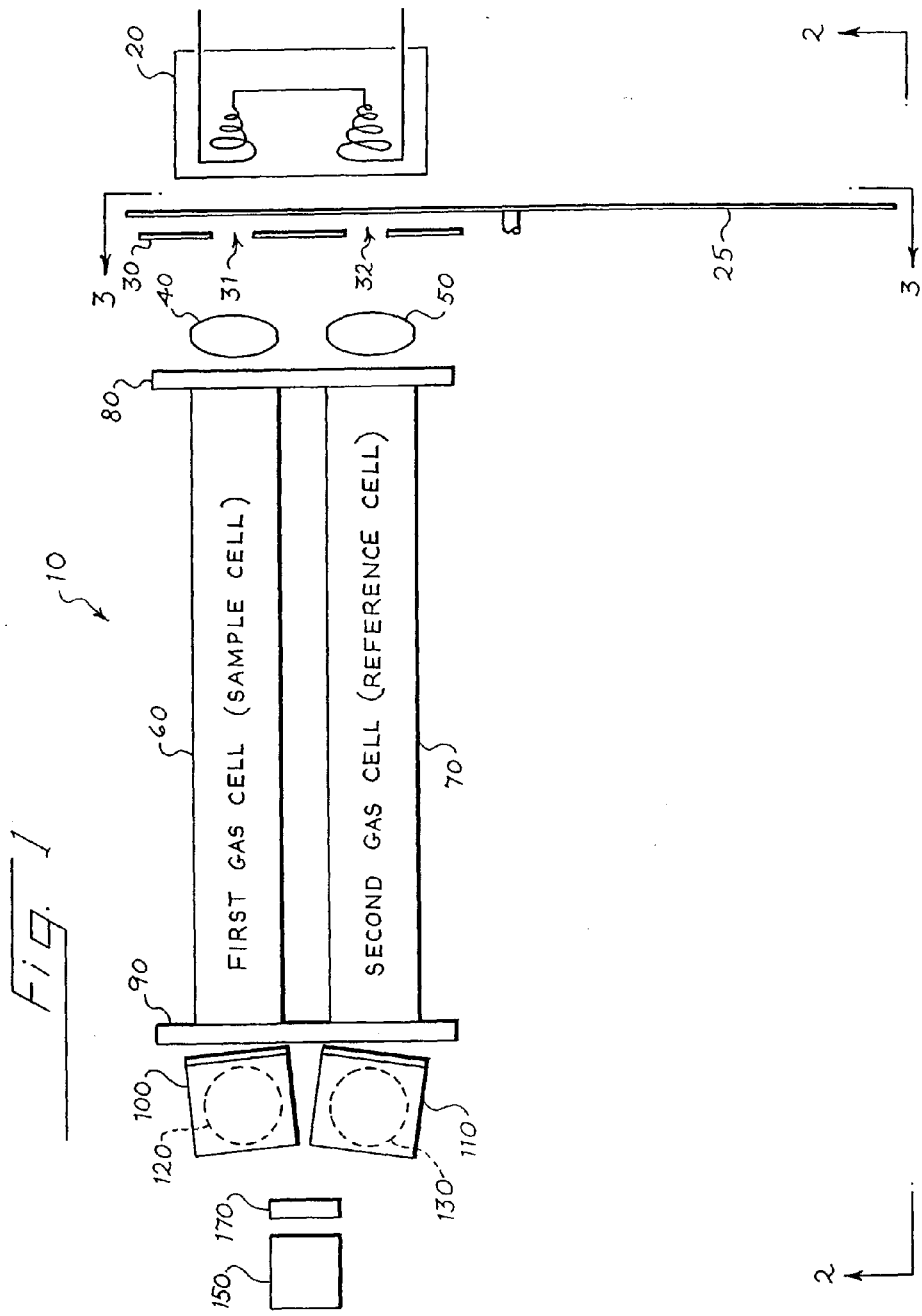

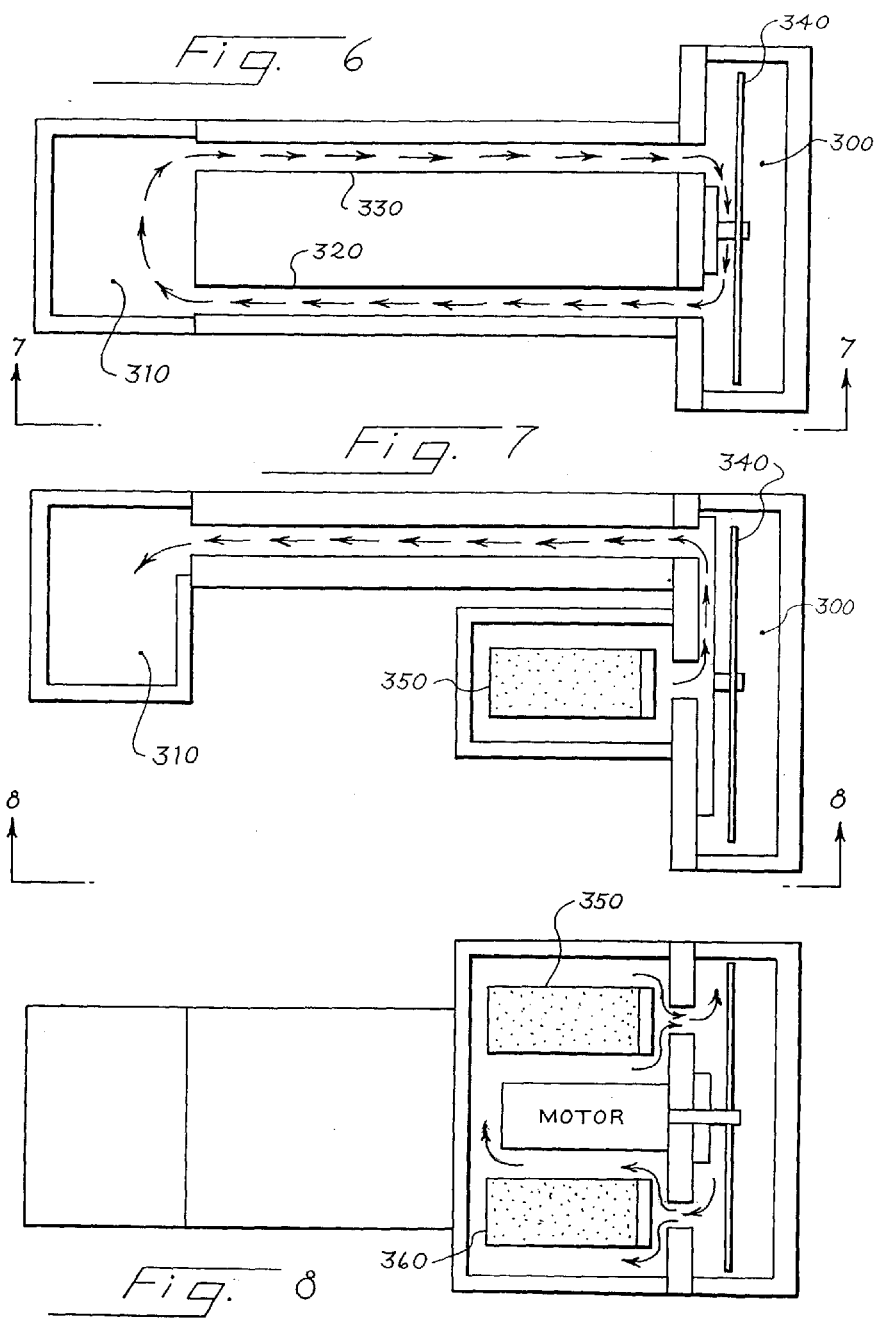

What is claimed is:

1. A gas analyzer comprising:
   a source section comprising a light source;
   a detector section comprising a detector;
   at least one gas cell disposed between the source and detector sections; and
   at least one purged gas flow channel coupling the source and detector sections, the at least one purged gas flow channel enabling purged gas to flow from one of the source and detector sections to the other of the source and detector sections.

2. The invention of claim 1 further comprising a scrubber located within one of the source or detector sections, the scrubber providing purged gas to said one of the source or detector sections.

3. The invention of claim 1 further comprising a scrubber located external to the source and detector sections, the scrubber providing purged gas to one of the source or detector sections.

4. The invention of claim 1 further comprising a desiccant located within one of the source or detector sections, the desiccant providing purged gas to said one of the source or detector sections.

5. The invention of claim 1 further comprising a desiccant located external to the source or detector sections, the desiccant providing purged gas to one of the source or detector sections.

6. The invention of claim 1 further comprising a purged gas circulation device located within one of the source or detector sections.

7. The invention of claim 6, wherein the purged gas circulation device comprises a rotating wheel comprising at least one opening formed therein.

8. The invention of claim 1 further comprising a purged gas circulation device located external to the source and detector sections.

9. The invention of claim 1, wherein the at least one purged gas flow channel comprises two purged gas flow channels.

10. The invention of claim 1, wherein the at least one gas cell comprises a sample gas cell and a reference gas cell.

11. In a gas analyzer comprising a light source, first and second gas cells, and a light disrupter disrupting transmission of light from the light source through the first and second gas cells, the improvement comprising:

a first lens disposed between the light source and the first gas cell;

a second lens disposed between the light source and the second gas cell;

a first spatial filter disposed between the light source and the first lens; and a second spatial filter disposed between the light source and the second lens;

wherein the first and second spatial filters position light from the light source on the first and second lenses, respectively, such that the first and second lenses transmit light through the first and second gas cells, respectively, without the light contacting an interior surface of the first and second gas cells.

12. The invention of claim 11, wherein at least one of the first and second spatial filters is disposed between the light source and the light disrupter.

13. The invention of claim 11, wherein at least one of the first and second spatial filters is disposed between the light disrupter and one of the first and second lens.

14. The invention of claim 11, wherein the light disrupter intermittently disposes a member between the light source and at least one of the first and second gas cells.

15. The invention of claim 11, wherein the light disrupter comprises a rotating wheel comprising at least one opening formed therein.

16. The invention of claim 11, wherein the light source transmits light having a spectrum of wavelengths including longer wavelengths and shorter wavelengths, and wherein the invention further comprises:

a beam splitter positioned to receive light transmitted through the first and second gas cells, the beam splitter having a high transmission for one of said longer and shorter wavelengths and a high reflectance of the other of said longer and shorter wavelengths;

a first detector positioned to receive light transmitted through the beam splitter; and a second detector positioned to receive light reflected from the beam splitter.

17. The invention of claim 16 further comprising a first narrow band pass filter between the beam splitter and the first detector, and a second narrow band pass filter between the beam splitter and the second detector, wherein the first narrow band pass filter passes only light of said longer wavelengths and wherein the second narrow band pass filter passes only light of said shorter wavelengths.

18. The invention of claim 17, wherein the first narrow band pass filter comprises a band pass filter centered around 4.25 $\mu$m and the second narrow band pass filter comprises a band pass filter centered around 2.59 $\mu$m.

19. The invention of claim 16, wherein at least one of the gas cells comprises a mixture of two gases, one of which having a high absorbance at said longer wavelengths and the other of which having a high absorbance at said shorter wavelengths; and wherein one of said detectors detects light within the high absorbance wavelength band of one of said gases and the other detector detects light within the high absorbance wavelength band of the other of said gases.

20. The invention of claim 19, wherein the high absorbance wavelength band of one of said gases is about 2.59 $\mu$m and wherein the high absorbance wavelength band of the other of said gases is about 4.25 $\mu$m.

21. The invention of claim 19, wherein the other of said at least one of the gas cells is substantially free of said two gases.

22. The invention of claim 16 further comprising a third lens disposed between the first gas cell and the beam splitter;

a fourth lens disposed between the second gas cell and the beam splitter;

a first mirror disposed between the first gas cell and the beam splitter; and a second mirror disposed between the second gas cell and the beam splitter;

wherein the first and second mirrors are positioned to direct light transmitted through the first and second gas cells, respectively, onto the beam splitter.

23. A gas analyzer comprising:

a source section;

a detector section;

first and second gas cells coupled with the source and detector sections;

a first window adjacent an end of the first and second gas cells proximate the source section;

a second window adjacent an end of the first and second gas cells proximate the detector section; and a set of sealing members disposed between the first and second windows and the first and second gas cells;

wherein the set of sealing members is formed to substantially prevent contaminants from entering the first and second gas cells when the first and second gas cells are disposed between the first and second windows and wherein the set of sealing members are further formed to allow the first and second gas cells to be removably disposed between the first and second windows.

24. The invention of claim 23 further comprising a housing, wherein the first and second gas cells are disposed in the housing and wherein the housing comprises at least one locator member allowing the first and second gas cells to be replaced in the gas analyzer without recalibrating the gas analyzer.

25. The invention of claim 23, wherein the set of sealing members comprises a first sealing member associated with a first end of the first and second gas cells and a second sealing member associated with a second end of the first and second gas cells.

26. The invention of claim 23, wherein the set of sealing members comprises a first sealing member associated with a first end of the first gas cell, a second sealing member associated with a second end of the first gas cell, a third sealing member associated with a first end of the second gas cell, and a fourth sealing member associated with a second end of the second gas cell.

27. The invention of claim 23, wherein the set of sealing members comprises an O-ring.

28. A gas analyzer comprising:

a housing;

first and second gas cells disposed in the housing;

a first air inlet portion disposed in the housing, the first air inlet portion allowing incoming air to flow into the first gas cell;

a second air inlet portion disposed in the housing, the second air inlet portion allowing incoming air to flow into the second gas cell;

a heat exchanger disposed in the first and second air inlet portions, the heat exchanger being operative to equilibrating a temperature of incoming air to a temperature of the housing.

29. The invention of claim 28, wherein the heat exchanger comprises a plurality of tubing compressed into the first and second air inlet portions.

30. The invention of claim 29, wherein the plurality of tubing comprises copper tubing.

31. The invention of claim 28, wherein the housing comprises an aluminum block.

32. The invention of claim 28 further comprising a light source positioned to transmit light having a spectrum of wavelengths including longer wavelengths and shorter wavelengths through the first and second gas cells disposed in the housing, and wherein the first air inlet portion is adapted to be connected to a source of a mixture of two gases, one of which having a high absorbance at said longer wavelengths and the other of which having a high absorbance at said shorter wavelengths.

33. The invention of claim 32, wherein the second air inlet portion is adapted to be connected to a source of air substantially free of said two gases.

34. The invention of claim 32, wherein the high absorbance wavelength bands of one of said gases is about 4.25 $\mu$m and wherein the high absorbance wavelength bands of the other of said gases is about 2.59 $\mu$m.

35. The invention of claim 28, wherein the housing is characterized by a large thermal mass.

* * * * *

UNITED STATES PATENT AND TRADEMARK OFFICE
CERTIFICATE OF CORRECTION

PATENT NO.    : 6,369,387 B1
DATED         : April 9, 2002
INVENTOR(S)   : Robert D. Eckles It is certified that error appears in the above-identified patent and that said Letters Patent is hereby corrected as shown below:

Title page,
Showing the illustrative figure should be deleted to be replaced with the attached title page.

Drawings,
Sheets 1-6, consisting of Figures 1-10, should be deleted to be replaced with the correct drawing Figures 1-10, as shown on the attached pages.

Signed and Sealed this

Sixteenth Day of July, 2002

*Attest:*

*Attesting Officer*

JAMES E. ROGAN
*Director of the United States Patent and Trademark Office*

(12) United States Patent
Eckles

(10) Patent No.: US 6,369,387 B1
(45) Date of Patent: Apr. 9, 2002

(54) GAS ANALYZER

(75) Inventor: Robert D. Eckles, Malcolm, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

(21) Appl. No.: 09/419,020

(22) Filed: Oct. 15, 1999

(51) Int. Cl.[7] .................... G01N 21/35; G01N 21/00

(52) U.S. Cl. ........................ 250/343; 250/345

(58) Field of Search .................... 250/343, 345

(56) References Cited

U.S. PATENT DOCUMENTS

| | | |
|---|---|---|
| 3,270,756 A | 9/1966 | Dryden |
| 3,712,325 A | 1/1973 | Harnoncourt |
| 3,792,272 A | 2/1974 | Harte et al. |
| 3,948,281 A | 4/1976 | Strain et al. |
| 4,355,234 A | 10/1982 | Fertig et al. |
| 4,395,632 A | 7/1983 | Röss et al. |
| 4,467,213 A | 8/1984 | Farren |
| 4,673,812 A | 6/1987 | Yoneda |
| 4,738,147 A | 4/1988 | Tomlin |

(List continued on next page.)

FOREIGN PATENT DOCUMENTS

| | | |
|---|---|---|
| DE | 3525346 | 1/1987 |
| DE | 199 11 260 A1 | 3/1999 |
| EP | 0503511 B1 | 5/1998 |
| JP | 54-13388 | 1/1979 |
| JP | 55-109948 | 8/1980 |
| JP | 59-173734 | 10/1984 |
| JP | 62-217139 | 9/1987 |
| WO | WO 98/45686 | 10/1998 |

OTHER PUBLICATIONS

English–Language Abstract for DE19911260A1 (2 pages).
Partial European Search Report and Annex for EP00307471 (3 pages).
Jones et al. A Fast Response Atmospheric $CO_2$ Sensor for Eddy Correlation Flux Measurements, *Atmospheric Environment*, vol. 12, pp. 845–851, Pergamon Press Ltd. 1978.
Bingham et al., Development of a Miniature, Rapid–Response Carbon Dioxide Sensor, Progress Report from the NSF Ecosystem Program, The National Science Foundation, (Project DEB 77–16327), Mar. 20, 1978.
Brach et al., Open Path $CO_2$ Analyser, *The Institute of Physics*, vol. 6, pp. 1415–1419, 1981.
Altmann et al., Two–Mirrow Multipass Absorption Cell, *Applied Optics*, vol. 20, No. 6, pp. 995–999, Mar. 15, 1981.

(List continued on next page.)

*Primary Examiner*—Constantine Hannaher
*Assistant Examiner*—Andrew Israel
(74) *Attorney, Agent, or Firm*—Brinks Hofer Gilson & Lione

(57) ABSTRACT

In one preferred embodiment, a gas analyzer is presented that focuses light beams through gas cells without reflecting the light beams off the walls of the cells. By eliminating wall reflections, dirt or debris on the walls of the cells will not result in inaccurate gas concentration measurements. In another preferred embodiment, a gas analyzer is disclosed having removable gas cells, which allows a user to easily clean the cells instead of returning a contaminated gas analyzer to service personnel for cleaning. In yet another preferred embodiment, a gas analyzer has a purged gas flow channel between source and detector sections of the analyzer to remove contaminants that can result in inaccurate gas concentration measurements. In an additional preferred embodiment, a gas analyzer is disclosed which has a heat exchanger to equilibrate the temperature of incoming air to the temperature of the analyzer's gas cells, thereby avoiding temperature-based errors in gas concentration measurements.

35 Claims, 6 Drawing Sheets